United States Patent [19]

Abelson

[11] Patent Number: 5,435,998
[45] Date of Patent: Jul. 25, 1995

[54] TREATMENT OF LOW-TENSION GLAUCOMA BY TOPICAL ADMINISTRATION OF CALCIUM CHANNEL BLOCKING AGENTS

[76] Inventor: Mark B. Abelson, 26 Phillips St., Andover, Mass. 01810

[21] Appl. No.: 285,301

[22] Filed: Aug. 3, 1994

[51] Int. Cl.$^6$ .......................................... A61K 31/135
[52] U.S. Cl. ................................ 424/78.04; 514/912; 514/913; 514/914; 514/915; 514/929; 424/427
[58] Field of Search ........................... 424/427, 78.04; 514/651, 912–915, 929

[56] References Cited

U.S. PATENT DOCUMENTS

| | | |
|---|---|---|
| 4,525,346 | 6/1985 | Stark ........................................ 424/80 |
| 4,753,802 | 6/1988 | Stephens et al. . |
| 4,981,871 | 1/1991 | Abelson ............................... 514/523 |

*Primary Examiner*—Thurman K. Page
*Assistant Examiner*—Sharon Howard
*Attorney, Agent, or Firm*—Vorys, Sater, Seymour & Pease

[57] ABSTRACT

Low-tension glaucoma is treated by topical administration to the eye of an amount of a calcium channel blocking agent effective to increase blood flow to the optic nerve head. Calcium channel blocking agents of Class I are especially useful, and among these a preferred agent is verapamil hydrochloride.

26 Claims, No Drawings

TREATMENT OF LOW-TENSION GLAUCOMA BY TOPICAL ADMINISTRATION OF CALCIUM CHANNEL BLOCKING AGENTS

BACKGROUND OF THE INVENTION

1. Field of the Invention

This invention relates to treatment of low-tension glaucoma by topically administered medications and more particularly to treatment of low-tension glaucoma by topical administration of calcium channel blocking agents.

2. Description of the Prior Art

Low-tension glaucoma is an ophthalmic condition in which the symptoms and ophthalmic pathology, i.e., loss of visual fields, loss of visual acuity and contrast sensitivity, cupping of the optic disk, etc., are present in the eye, but the intraocular pressure (IOP) is normal or only slightly elevated. It is distinguishable from primary open angle glaucoma, which is characterized by an elevated IOP. The etiology of the disease is not well understood and consequently there is no consensus as to a medicinal course of therapy. While available topical therapy may lower IOP, it is not been conclusively demonstrated to alter beneficially the course of the disease.

Consequently, certain topical medications have been used in an attempt to delay the progression of ophthalmic deterioration or even partially reverse the course of the disease. Nevertheless, conventional ophthalmic medications that lower the IOP have been used in an attempt to maintain the IOP as low as possible, even somewhat below the range usually considered as normal. Systemic drugs that increase the blood flow to the optic nerve head and/or retina have been found to have some effect in alleviating the loss of visual function in low-tension glaucoma. In particular, systemic, e.g., oral, administration of calcium channel blocking agents has been found on occasion to be of benefit in low-tension glaucoma. However, the systemic administration of vasoactive drugs in order to treat a condition of the optic nerve head and/or retina is subject to the evident disadvantage that it is difficult to attain sufficient ocular concentration without inducing systemic adverse side effects. Hitherto it has not been known to increase blood flow to the optic nerve head and/or retina and thereby arrest or alleviate the deterioration associated with low-tension glaucoma by topical administration of drugs to the eye.

Although it is well known to apply topical medications to treat ophthalmic disorders caused by dysfunction of tissues in the anterior region of the eye, topical application of medication has not been generally found effective to treat ophthalmic pathologic conditions of tissues and structures located in the posterior segment of the eye.

Accordingly, a need has continued to exist for a method of treating low-tension glaucoma by topical administration of an effective ophthalmic medicament.

SUMMARY OF THE INVENTION

This need has now been met by the method of the invention according to which low-tension glaucoma is treated by topical administration to the eye of a human or mammal afflicted with low-tension glaucoma of an amount of a calcium channel blocking agent effective to increase blood flow to the optic nerve head and/or retina.

Accordingly, it is an object of the invention to provide a method for treatment of low-tension glaucoma.

A further object is to provide a method for treatment of low-tension glaucoma by topical administration of a drug that increases blood flow to the optic nerve head and/or retina.

A further object is to provide a method for treatment of low-tension glaucoma by topical administration of a calcium channel blocking agent.

A further object is to provide a method for treatment of low-tension glaucoma by topical administration of a calcium channel blocking agent in a formulation that is safe to tissue at the site of topical application and to any tissue involved in the pharmacological response.

A further object is to provide a method for treatment of low-tension glaucoma by topical administration of a calcium channel blocking agent in a formulation that is safe for chronic therapy.

A further object is to provide a method for treatment of low-tension glaucoma by topical administration of a calcium channel blocking agent in a formulation that minimizes discomfort upon application.

A further object is to provide a method for treatment of low-tension glaucoma by topical administration of a calcium channel blocking agent in a formulation that supports good chronic patient compliance.

Other objects will become apparent from the description of the invention which follows.

DETAILED DESCRIPTION OF THE INVENTION AND PREFERRED EMBODIMENTS

According to the invention, the pathological ophthalmic conditions associated with low-tension glaucoma are alleviated, or the progressive deterioration in ophthalmic function delayed by topical administration of an amount of a calcium channel blocking agent effective to increase optic nerve blood flow in the eye. The increase in optic nerve blood flow produced by topical application of calcium channel blocking agents can stop or reverse the loss in visual function as measured by, but not limited to, contrast sensitivity, visual acuity and/or visual fields associated with low-tension glaucoma.

Calcium channel blocking agents are currently classified into six classes, based on the physiological effect produced by systemic administration. Class I calcium channel blocking agents include verapamil, gallopamil, anipamil and the like. Class II agents include nifedipine, nicardipine, nimodipine, nitrendipine and the like. Class III agents include diltiazem and compounds with similar activity. Class IV agents include flunarizine, cinnarizine and the like. Class V agents include prenylamine, fendiline and the like. Class VI agents include perhexiline and compounds having similar activity.

Preferred calcium channel blocking agents are those of Class I. Within Class I a preferred calcium channel blocking agent is verapamil. The verapamil molecule contains a basic nitrogen atom and, accordingly, verapamil may be administered in the free base form or in the form of an acid addition salt with a pharmacologically acceptable non-toxic acid, e.g., as the hydrochloride salt. A preferred form verapamil for topical administration is verapamil hydrochloride. Verapamil hydrochloride may be administered in an aqueous solution containing from about 0.01% to about 1.0% by weight of the active ingredient. Preferably verapamil hydrochloride is administered in an aqueous solution containing 0.25% of verapamil hydrochloride by weight.

The effective dose of calcium channel blocking agent used in the method of this invention will vary depending on the particular patient, the particular calcium channel blocking agent used and the mode of administration. The topical dose applied by instillation into the eye will typically range from about 10 micrograms to about 10 milligrams per eye per day. The topical dose will generally be applied by instillation of the drug in a suitable vehicle 2-4 times per day.

The calcium channel blocking agent may be administered topically in a dosage form comprising a solution or suspension of the drug in any conventional aqueous pharmaceutically acceptable ophthalmic vehicle. Such vehicles are well known to those skilled in the art, and include hydrophilic and hydrophobic media for dissolving or suspending the drugs.

The hydrophilic media include aqueous solutions and water-miscible ointments in which the drugs may be dissolved or suspended in finely divided form. The aqueous solutions and suspensions may incorporate pharmaceutically acceptable auxiliary ingredients that are not incompatible with the drug.

A suitable vehicle may comprise a simple physiological saline solution containing 0.9% sodium chloride by weight. Such a solution is isotonic with the tear fluid and is therefore non-irritating to the eye. Other solutions or suspensions wherein the formulation including the drug and other auxiliary ingredients is hypotonic may be adjusted to isotonicity by addition of a tonicity adjusting agent, e.g., sodium chloride. However, hypotonic and hypertonic solutions or suspensions may also be used, as it is known that certain hypotonic or hypertonic solutions are also acceptable for compliant ocular use.

The ophthalmic solutions and suspensions may incorporate other auxiliary agents such as buffers to control the pH within the practical range for storing and applying topical ophthalmic drugs, i.e, from about pH 3 to about pH 8.5. For example, a physiological saline solution may be buffered with a suitable buffering agent, e.g., a phosphate buffer, to maintain approximately physiological pH. Such a solution may be buffered at a pH of 7.2-7.4 to match the natural pH of the tears bathing the anterior segment of the eyeball.

Furthermore, it will be recognized by those skilled in the art that some ophthalmic drugs must be stored and distributed at a pH different from that of the tear fluid. For example, some drugs containing basic nitrogen atoms must be stored in the form of their acid addition salts at an acidic pH, e.g., pH 3-5, in order to have an adequate shelf life. For such solutions, conventional buffers capable of maintaining such a pH are used, e.g., acetate buffers, citrate buffers, ascorbate buffers, phosphate buffers or boric acid buffers.

The ophthalmic solution or suspension may incorporate conventional ingredients to improve the comfort of the dosage form, e.g., demulcents, such as polysorbate 80, polyethylene glycol (PEG) 400, dextran 70, gelatin, glycerin, propylene glycol, and the like. The ophthalmic solution or suspension may contain viscosity increasing constituents such as methylcellulose, hydroxypropyl cellulose, hydroxypropyl methylcellulose, poly(vinylpyrrolidone), polyvinyl alcohol, and the like. Several of the viscosity-adjusting agents also exhibit a demulcent function. Many of the viscosity-adjusting agents, when used as constituents of suspensions or emulsions containing the active ingredient, act as suspending agents to retard settling of solid particles or as protective colloids for emulsions to prevent phase separation.

The ophthalmic vehicle, whether hydrophilic or hydrophobic, may also incorporate conventional antimicrobial preservative agents in order to prevent contamination of multiple-dose packages of the ophthalmic medication such as dropping bottles, tubes of ointments or bottles with accompanying eyedroppers. Suitable preservatives include quaternary ammonium compounds, e.g., benzalkonium chloride, cetylpyridinium chloride and the like; ethyl paraben, propyl paraben; alcohols, such as benzyl alcohol; organomercurial compounds, such as thimerosal; polybiguanide compounds such as chlorhexidine digluconate, polyaminopropyl biguanide, and the like.

A compound that promotes the permeation of the drug into the ocular tissues, such as dimethyl sulfoxide, a quaternary ammonium compound, e.g., benzalkonium chloride, or an ophthalmologically acceptable surfactant, e.g., disodium lauryl sulfosuccinate, or the like may also be incorporated into the ophthalmic vehicle. When the drug is administered in the form of a suspension in an aqueous medium the suspension may also contain a suspending agent, e.g., methyl cellulose, propylcellulose, carboxymethyl-cellulose, poly(vinylpyrrolidone), poly(vinyl alcohol), and the like.

Among the water-miscible ointments and jellies usable as vehicles for the calcium channel blocking agents are polyethylene glycols, e.g., mixtures of low molecular weight PEGs and relatively high molecular weight PEGs, acrylic acid polymers, polyoxyethylene derivatives of fatty carboxylic acids and fatty alcohols, and the like.

Among the hydrophobic media suitable as vehicles for topical administration of calcium channel blocking agents according to the invention are ointments and oil-in-water or water-in-oil emulsions wherein the active ingredient is contained in an oleaginous phase which may comprise petrolatum, white petrolatum, light, medium and heavy grades of mineral oil, hydrous lanolin, anhydrous lanolin, paraffin, white wax, yellow wax, white ointment, or the like.

Typically, the concentration of the calcium channel blocking agent in the vehicle will vary from about 0.1 mg/ml to about 60 mg/ml, or from about 0.01% by weight to about 6.0% by weight. When the drug is delivered in an aqueous solution, the concentration of the drug is preferably adjusted to deliver the desired dose of active ingredient in a single drop. Because of the limited size of the conjunctival sac into which the drop of solution is instilled, and the presence of the normal amount of tear fluid in the sac, the amount of drug solution that can be instilled without causing discomfort and/or overflow is limited. The amount should not ordinarily exceed 50 microliters. A conventional eyedropper forms drops of about 40 microliters, but even this amount often cannot be fully accepted by the conjunctival sac, and some overflow may occur. Accordingly, the concentration of the solution should be adjusted so that the amount of drug solution actually retained within the conjunctival sac after instillation contains an effective dose of medication. If a smaller volume of solution is instilled, e.g., a volume of about 15 microliters, little or no drug will be lost by overflow, and the discomfort generally associated with ocular administration of medication may be decreased. When such smaller volumes are administered the concentration of the solution is adjusted to provide an effective dose in the volume administered, e.g., a 15 microliter volume of solution.

When the calcium channel blocking agent is applied to the eye in ointment form, the ointment may be simply applied to the lower segment of the eye within the lower eyelid.

The calcium channel blocking agent may be delivered to the eye on any dosage schedule that is found to be effective. Typically the dosage schedule is determined by the duration of effectiveness of the particular active agent. For example, the dosage regimen may comprise one drop of an aqueous solution of the calcium channel blocking agent instilled into the affected eye from one to four times per day.

Topical administration of the calcium channel blocking agent may also be carried out by means of a controlled release dosage form inserted into the eye. Such devices are well known in the art and may comprise, e.g., a dispersion or solution of the drug in a polymeric matrix which is formed into a suitable lamella and inserted into the cul-de-sac of the conjunctiva where it slowly releases the medication over a period of time until the matrix is dissolved or removed after the drug is exhausted.

A preferred ophthalmic solution for practicing the method of the invention comprises verapamil hydrochloride dissolved in an aqueous solution containing an acidifying agent, e.g., boric acid, to adjust the pH to a range of about 4.5-5.5, and at least one buffer having a buffering range between the pH of the solution and the normal pH of the tear fluid bathing the eye. A more preferred ophthalmic solution for topical application of verapamil according to the invention contains the following buffers in the specified concentration ranges, wherein all percentages are by weight:

| | |
|---|---|
| boric acid | 0.5-3.0% |
| disodium edetate | 0.08-0.5% |
| dextrose | 0.1-5.0% |
| poly(vinylpyrrolidone) (PVP) | 1.0-4.0% |
| water, q.s. ad | 100% |

A particularly preferred formulation of the invention comprises verapamil HCl in an aqueous solution of the following ingredients, wherein all percentages are by weight:

| | |
|---|---|
| boric acid | 2.8% |
| disodium edetate | 0.18% |
| dextrose | 0.3% |
| poly(vinylpyrrolidone) (PVP) | 2.0% |
| water, q.s. ad | 100% |

Additionally, benzalkonium chloride (BAC) can be included in the ophthalmic solution as an antimicrobial agent to maintain the sterility of the packaged solution in multidose containers. If the solution is packaged in unit-of-use (one time use containers), the BAC may be omitted from the formulation.

EXAMPLE

This example illustrates the improvement of blood flow to the optic nerve head and retina in humans produced by topical administration of verapamil hydrochloride.

Blood flow in the optic nerve head of human volunteers having normal IOP was measured by the laser doppler technique. A group of 10 individual, after informed consent, was tested in a randomized double blind study by the following procedure.

For each experimental subject, before administration of the drug or control solution, the IOP was measured and the blood flow in the central retinal artery was examined by the laser doppler flow measurement technique and the mean Pourcelot's ratio, a measure of vascular resistance of the central retinal artery was determined. Subsequently, one drop of a 0.25% by weight solution of verapamil hydrochloride in an aqueous ophthalmic vehicle was instilled into an eye of each subject. Two hours after administration, the IOP and blood flow in the central retinal artery at the level of the optic nerve head were again measured.

It was found that for the treated experimental subjects the mean Pourcelot's ratio was $0.77 \pm 0.02$, which represents a reduction of $0.10 \pm 0.03$ for the treated eyes as compared with a reduction of $0.02 \pm 0.03$ for the untreated eyes. These results establish that topical administration of verapamil hydrochloride produces a significant reduction in the vascular resistance of the central retinal artery, and, consequently, increased blood flow to the optic nerve head. A mean reduction in IOP for the treated eyes of 11% was also observed.

This experiment establishes that the topical administration of a calcium channel blocking agent can effectively increase blood flow to the optic nerve head and/or retina and thereby alleviate the damage to the structure and function of the eye that is characteristic of low-tension glaucoma, indicating its ability to penetrate to the back of the eye sufficiently to induce a physiological effect in a formulation tolerable for chronic ophthalmic use.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A method for treating low-tension glaucoma comprising topically administering to the eye of a human or mammal afflicted with low-tension glaucoma an amount of a Class I calcium channel blocking agent which is effective to increase blood flow to the optic nerve head.

2. The method of claim 1 wherein said calcium channel blocking agent is verapamil or a pharmaceutically acceptable non-toxic acid addition salt thereof.

3. The method of claim 2 wherein said calcium channel blocking agent is a verapamil in the form of a pharmaceutically acceptable non-toxic acid addition salt.

4. The method of claim 3 wherein said calcium channel blocking agent is verapamil hydrochloride.

5. The method of claim 2 wherein said calcium channel blocking agent is verapamil in the free base form.

6. The method of claim 1 wherein said Class I calcium channel blocking agent is administered in a dosage form comprising an ophthalmologically acceptable vehicle containing an amount of said calcium channel blocking agent effective to increase blood flow to the optic nerve head.

7. The method of claims 6 wherein said dosage form is an aqueous ophthalmic dosage form.

8. The method of claim 7 wherein said dosage form is an aqueous solution.

9. The method of claim 7 wherein said dosage form is an aqueous suspension.

10. The method of claim 7 wherein said dosage form is an aqueous emulsion.

11. The method of claim 7 wherein said aqueous ophthalmic dosage form is isotonic.

12. The method of claim 7 wherein said aqueous ophthalmic dosage form is hypotonic.

13. The method of claim 7 wherein said aqueous ophthalmic dosage form is hypertonic.

14. The method of claim 7 wherein said aqueous ophthalmic dosage form additionally comprises a buffer.

15. The method of claim 7 wherein said aqueous ophthalmic dosage form additionally comprises a viscosity adjusting agent.

16. The method of claim 7 wherein said aqueous ophthalmic dosage form additionally comprises a demulcent.

17. The method of claim 7 wherein said aqueous ophthalmic dosage form additionally comprises an agent that increases tissue permeability.

18. The method of claim 7 wherein said aqueous ophthalmic dosage form additionally comprises an antimicrobial preservative.

19. The method of claim 9 wherein said aqueous suspension contains a suspending agent.

20. The method of claim 8 wherein said Class I calcium channel blocking agent is verapamil or a pharmacologically acceptable non-toxic acid addition salt thereof administered in an aqueous ophthalmic solution comprising an amount of a ophthalmologically acceptable acidifying agent sufficient to maintain the pH of said solution at an acidic pH in the range of 4.5–5.5 during storage, and an amount of an ophthalmologically acceptable buffer having a pH buffering range between the pH of the solution and the normal pH of the mammalian eye sufficient to cause a gradual neutralization of the solution by the tears of the eye when a dose of the ophthalmic solution is instilled into the eye.

21. The method of claim 20 wherein said Class I calcium channel blocking agent is administered in an aqueous ophthalmic solution comprising

| boric acid | 0.5–3.0% by weight |
| disodium edetate | 0.08–0.5% by weight |
| dextrose | 0.1–5.0% by weight |
| poly(vinylpyrrolidone) | 1.0–4.0% by weight. |

22. The method of claim 21 wherein said aqueous ophthalmic solution additionally comprises an amount of an ophthalmologically acceptable antimicrobial compound sufficient to preserve said aqueous ophthalmic solution from microbial contamination.

23. The method of claim 22 wherein said ophthalmologically acceptable antimicrobial compound is benzalkonium chloride.

24. The method of claim 21 wherein said aqueous opthalmic solution comprises

| boric acid | 2.8% by weight |
| disodium edetate | 0.18% by weight |
| dextrose | 0.3% by weight |
| poly(vinylpyrrolidone) | 2.0% by weight. |

25. The method of claim 24 wherein said aqueous ophthalmic solution additionally comprises an amount of an ophthalmologically acceptable antimicrobial compound sufficient to preserve said aqueous ophthalmic solution from bacterial contamination.

26. The method of claim 25 wherein said ophthalmologically acceptable antimicrobial compound is benzalkonium chloride.

* * * * *